United States Patent [19]

Celebuski

[11] Patent Number: 5,113,005

[45] Date of Patent: May 12, 1992

[54] PROCESS FOR SYNTHESIS OF SILYL ALCOHOLS

[75] Inventor: Joseph E. Celebuski, Gurnee, Ill.

[73] Assignee: Abbott Laboratories, Abbott Park, Ill.

[21] Appl. No.: 712,020

[22] Filed: Jun. 7, 1991

[51] Int. Cl.$^5$ ................................. C07F 7/08
[52] U.S. Cl. .................................. 556/449
[58] Field of Search ......................... 556/449

[56] References Cited

U.S. PATENT DOCUMENTS 4,689,383  8/1987  Riffle et al. ............... 556/449 X

OTHER PUBLICATIONS

Kumada et al., *J. Organometal Chem.* 6:490–495 (1966).
Seyferth, *J. Am. Chem. Soc.* 81:1844 (1959).
Fessenden et al., *J. Org. Chem.* 32:3535 (1967).
Collman et al., Principles and Applications of Organotransition Metal Chemistry, University Science Books (1980) pp. 384–389.
Pegram et al., *Carbohydrate Research* 184:276 (1988).
Salimgareeva et al., *Zh. Obshch. Khim* 48(4):930–931 (1978) (Russian).
Salimgareeva et al., C.A. 89:146961y.
Honda et al., *Tetrahedron Letters*, 22(22):2093–2096 (1981).
Lesage et al., *J. Org. Chem.*, 55:5413 (1990).

*Primary Examiner*—Paul F. Shaver
*Attorney, Agent, or Firm*—Thomas D. Brainard

[57] ABSTRACT

Novel silyl alcohols having bulky substituents bonded to the silicon, and the silyl group attached to a carbon include the preferred 2-silyl-ethan-1-ols. A method for synthesizing silyl substituted alcohols include hydrosilation of a vinylic ester, especially vinyl acetate, followed by hydrolysis in mild base. The silyl alcohols are useful in preparing phosphorylating reagents for phosphorylating an oligonucleotide. The phosphorylated intermediate bearing the silyl group may be separated from failure product on the basis of bulky substituents on the silyl protecting group, which is later removed, e.g. by fluoride ion.

18 Claims, 2 Drawing Sheets

PROCESS FOR SYNTHESIS OF SILYL ALCOHOLS

The invention relates generally to silyl alcohols, their synthesis, and their use. More specifically, the invention relates to specific silyl alcohols and to a method for synthesizing silyl alcohols having the silicon atom bonded to a carbon rather than to the hydroxyl. The invention also relates to reagents and methods for phosphorylating oligonucleotides, and to intermediate compounds and methods useful for purification of phosphorylated oligonucleotides.

This application is related to co-owned and co-pending applications Ser. Nos. 07/712,001, filed Jun. 7, 1991 and 07/712,302 filed Jun. 7, 1991, each of which is incorporated herein by reference.

BACKGROUND

Chemically synthesized oligonucleotides have been used in hybridization assays for some time, and by now are fairly routine. However, for uses which imitate biological processes, e.g. hybridizations of nucleic acid probes on a template followed by ligation, the normal 5' hydroxyl terminus must be converted to a phosphate to provide the proper substrate for a ligase. Methods of phosphorylating include enzymatic and synthetic as described below. The present invention describes a particular synthetic method, wherein silyl substituted alcohols are useful reagents.

Synthesis of silyl substituted alcohols has been previously achieved by oxidation of organoboranes. The organoboranes are in turn prepared by the Grignard reaction or by hydroboration of vinyl- and allyl-silanes. This technique is described in Kumada, et al. *J. Organometal. Chem.* 6: 490-495 (1966) and Seyferth, *J. Am. Chem. Soc.* 81: 1844 (1959). This technique is useful only when the requisite vinyl or allylsilanes can be synthesized or obtained commercially. However, if the desired vinyl silane is commercially unavailable or difficult to synthesize this method is not useful.

Alpha silyl esters have been prepared by reacting a chlorosilane and an alpha-bromo ester with zinc under Reformatsky conditions. See Fessenden, et al., *J. Org. Chem.* 32: 3535 (1967).

An important drawback of these synthesis methods is the side reactions which can occur leading to undesirable products and decreasing the yields. In conventional processes for hydrolyzing silyl substituted esters to the corresponding silyl substituted alcohol, a carbanion intermediate is generally formed. With β-silyl substituted alcohols, fragmentation to the silanol and an olefin can occur; with alpha silyl substituted alcohols, a Brook rearrangement to give a silyl protected ether will occur. Thus, in these carbanion intermediates there is a strong tendency for an elimination reaction whereby the silicon atom shifts to the oxygen atom to form the $R_3SiOH$ byproduct. This tendency is especially pronounced when the reaction is performed in strong base and when groups substituted on the silicon are particularly bulky.

Hydrosilation, the addition of H and silyl compounds across the double bond of an olefin, has also been described in the literature. See Collman, et al. *Principles and Applications of Organotransition Metal Chemistry*, University Science Books (1980) p. 384-389 and Pegram, et al. *Carbohydrate Research* 184: 276 (1988). In a particularly relevant hydrosilation reaction, Salimgareeva, et al., *Zh. Obshch. Khim* 48(4): 930-31 (1978)(Russian) (see also C.A. 89: 146961y) report hydrosilation of vinyl acetate with dimethylsilane. This reaction resulted in two silyl substituted products: a monoacetate and a diacetate. The reference fails to describe synthesis of any silyl alcohol or the use or synthesis of any bulky silyl substituted compound.

Honda, et al. *Tetrahedron Letters*, 22(22): 2093-2096 (1981) describe a β-silyl substituted ethanol wherein the silyl group bears two phenyl and one methyl substituent. Honda, et al. used this compound to prepare a phosphorylating agent which places a protected phosphate group between nucleotides in oligonucleotide synthesis. The substituted silyl protecting group can be removed to give a silyl fluoride compound, ethylene and the phosphate. The substituted silyl ethanol was obtained by reduction of the bisphenylmethyl silyl acetate with $LiAlH_4$ according to a modification of the procedure of Gerlach, *Helv Chim. Acta*, 60: 3039 (1977).

Other silyl substituted ethanols have been described in the literature, but primarily include alkyl substituted silyl groups. Examples of such silyl ethanols and their literature citations are found in the following table.

TABLE 1

$$R'-\underset{\underset{R''}{|}}{\overset{\overset{R}{|}}{Si}}-CH_2-CH_2-OH = \text{GENERAL STRUCTURE}$$

| R | R' | R" | Literature Citation |
|---|---|---|---|
| isopropyl | isopropyl | isopropyl | CA111(11):97352n |
| methyl | methyl | propenyl | CA105(13):115112s |
|  |  |  | CA108(17):150554w |
| methyl | n-butyl | n-butyl | CA88(3)23391j; |
|  |  |  | CA83(11):97563k; |
|  |  |  | CA78(15):93640g; & |
|  |  |  | CA78(13):84526x |
| methyl | methyl | t-butyl | CAOLD (prior to 1967) |
| ethyl | ethyl | ethyl | CA111(11):973552n; |
|  |  |  | CA98(9):72207u; |
|  |  |  | CA87(15):117488c; |
|  |  |  | CA85(21):154709e; |
|  |  |  | CA80(11):59132z; & |
|  |  |  | CA77(18):120049a |
| propyl | propyl | propyl | CA103(19):160573n |
| phenyl | phenyl | methyl | Honda, et al., Tetrahedron Letters, 22(22):2093-2096 (1981) |

Triphenyl silane (not the alcohol) has been described by Lesage, et al. *J. Org. Chem* 55: 5413 (1990) as a useful reducing agent.

In addition to the method of Honda, et al. (See above), several methods for phosphorylating the 5' terminus of an oligonucleotide are known. Initially, enzymatic methods using polynucleotide kinase were employed after the oligonucleotide was synthesized and removed from the solid support. Others have taught methods and reagents for chemically phosphorylating a synthesized oligonucleotide prior to its removal from the solid support. Some of these are described below.

Kondo, et al. *Nucl. Acids Res. Symposium Series* 16: 161-164 (1985) describe phosphotriester (1) and phosphoramidite (2) reagents for phosphorylating 5' termini. Phosphorylation is achieved by preparing a special diphosphorylated (3'-5') nucleotide which is added as the last nucleotide in the chain. The 3' phosphate is linked via the phosphotriester or phosphoramidite to the extending nucleotide chain. The 5' phosphate is protected with a protecting group which is ultimately removed.

Uhlmann, et al. *Tetrahedron Letters* 27(9): 1023-1026 (1986) describe a phosphoramidite phosphorylating reagent using a p-nitrophenylethyl group as a blocking group. They mention that the hydrophobic p-nitrophenylethyl is advantageous in that phosphorylated compounds can be separated from non-phosphorylated compounds by reversed phase HPLC.

Uhlmann, et al, however, used only hexamers to which the p-nitrophenylethyl "handle" was attached. A similar approach using a p-nitrophenylethyl handle with 20-mers is described by G. Zon in chapter 14 of *HPLC in Biotechnology*, (W. S. Hancock, ed), J. Wiley & Sons, New York, N.Y. pp 359–363 (1990). The purification results obtained by Zon with this method are marginal.

Marugg, et al. *Nucl. Acids Res.* 12(22): 8639–8651 (1984) describe a new phosphorylating agent, 2-cyano-1,1-dimethylethoxy dichlorophosphine. This agent has the alleged advantage of being removed under just basic conditions.

Himmelsbach, et al. *Tetrahedron Letters* 23(46): 4793–4796 (1982) describe a new phosphorylating agent, bis-(p-nitrophenylethyl) phosphoromonochloridate. Van der Marel, et al. *Tetrahedron Letters*, 22(19): 1463–1466 (1981) describe a morpholino phosphoro bis-3-nitro-1, 2, 4-triazolidate.

Horn, et al. *Tetrahedron Letters* 27 (39): 4705–4708 (1986) describe a phosphorylating reagent including a 4, 4' dimethoxytrityl group which, upon release, can be used to monitor the efficiency of phosphorylation. This disclosure appears to be quite similar to that of EP-A-304 215 and to the commercially available Clontech product known as 5' Phosphate-On.

Lipshutz, et al. *Tetrahedron Letters* 30(51): 7149–7152 (1989) ("Lipshutz 1989") and Lipshutz, et al. *Tetrahedron Letters* 21: 3343–3346 (1980) ("Lipschutz 1980") and Von Peter Sieber, *Helvetica Chimica Acta* 60: 2711 (1977) all disclose the use of fluoride in the removal of a silyl protecting group. In this regard, they are similar to Honda, et al. (See above).

While each of the above reagents and methods are adequate for phosphorylating synthesized oligonucleotides, each has draw backs as well. For example, each of the recited references discloses a method for removing the phosphate blocking group to generate the native 5' phosphate. Some (e.g. Horn, et al.) describe a blocking agent having a detectable characteristic (e.g. color) by which the extent of phosphorylation can be monitored. While the extent of phosphorylation can be monitored by this means, it provides no means for purification. Uhlmann, et al. suggest that the hydrophobic p-nitrophenylethyl group can be used prior to cleavage to separate phosphorylated hexamers by HPLC. The protected hexamers cited by Uhlmann, having a relatively low molecule/protecting group mass ratio, are generally too short to provide specificity necessary in hybridization assays.

However, none of the references teach phosphorylating/blocking reagents comprising silyl substitutes. Further, none suggest that the silyl protecting group can be used to purify phosphorylated nucleotides from unphosphorylated failure product. The present invention seeks to overcome these disadvantages.

SUMMARY OF THE INVENTION

In a first aspect, the invention relates to a process for synthesis of silyl alcohols, comprising:
a) hydrosilation of an vinylic ester of the formula

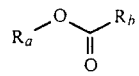

wherein $R_a$, is a straight or branched alkenyl group having from 2 to about 20 carbons and $R_b$ is H or lower alkyl, with a silane of the formula

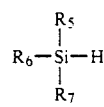

wherein $R_5$, $R_6$ and $R_7$ are independently selected from the group consisting of H, alkyl, aryl, substituted alkyl, substituted aryl, oxa and thia analogs of alkyl, aryl, substituted alkyl and substituted aryl, and halogen, in the presence of a metal catalyst capable of catalyzing the addition of H and a silyl group across the double bond of the alkenyl group to form a silyl substituted ester; and
b) hydrolyzing the silyl substituted ester to an alcohol in the presence of mild base.

Generally, $R_a$ is lower alkenyl; preferably $R_a$ is vinyl. Generally, $R_b$ is lower alkyl; preferably methyl. For use as a phosphorylating reagent, at least one of $R_5$, $R_6$ and $R_7$, preferably more than one, should consist of a sterically bulky, and ideally a hydrophobic, group.

Preferably, hydrosilation is done in a solution of toluene ranging from about 0.1 to about 4 molar, especially about 1 molar. The metal catalyst is usually a transition metal complex having a metal selected from the group consisting of cobalt, nickel, platinum, palladium and rhodium, for example, $\{RhCl(CO)_2\}_2$. Hydrolysis is usually done in a protic solvent such as methanol or ethanol with a mild base such as $K_2CO_3$.

The process may further comprise a step of separating the silyl substituted alcohol from undesired products of side reactions, for example, by chromatography.

DETAILED DESCRIPTION

A. General Definitions

Figure 1:
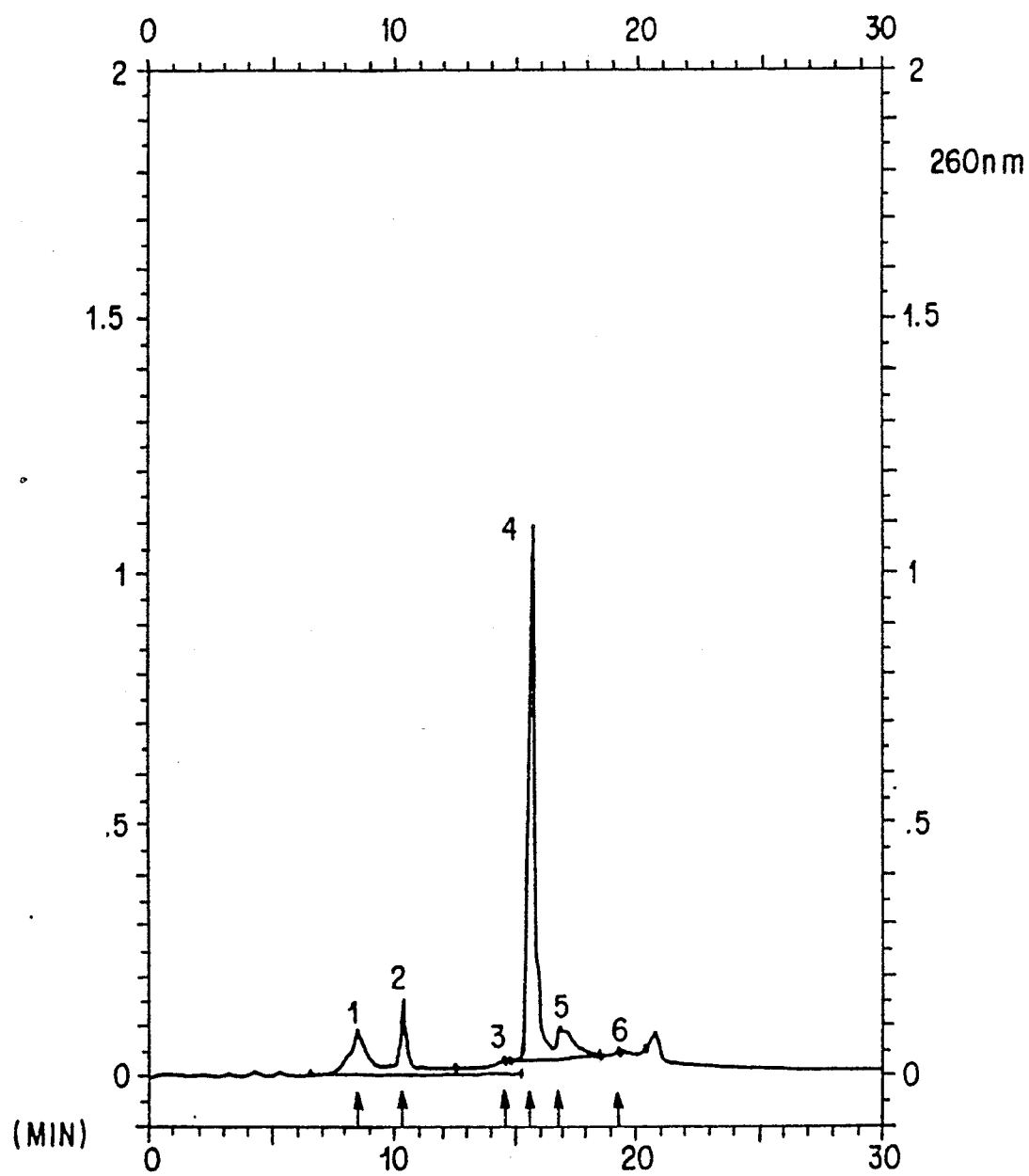
FIG. 1 is a chromatogram showing separation of a phosphorylated oligonucleotide (peak 4 at 15.5 min) from the failure products (peak 1 at 8.4 min). The chromatogram was generated from a Waters μBondapak TM C18 column, 3.9 mm × 150 mm flowing at 1.5 mL/min. Solvent A was 100 mM Triethylammonium Acetate and solvent B was Acetonitrile. Solvents were mixed according to a linear gradient table such that the ratio of A:B was as follows: At time=0, 90:10; at time=15 min, 60:40; at time=25, 60:40; and at time=30, 90:10. Detection was in absorbance units at 260 nm. (See Example 9a.)

In general, terms like "alkyl", "alkenyl" and "aryl" have the meanings usually attributed to them by persons skilled in the art of organic chemistry. For example, alkyl refers generally to monovalent straight or branched aliphatic radicals which may be derived from alkanes by the removal of one hydrogen, and have the general formula $C_nH_{2n+1}$. Alkyl groups may have from 1 to about 30 carbons, more practically 1 to about 15 or 20. "Lower alkyl" refers to alkyls having from 1 to about 6 carbons. Examples of lower alkyl include $CH_3$—, $CH_3CH_2$—, $CH_3CH(CH_3)$—, and $CH_3(CH_2)_4$—. As used herein, "alkyl" includes cycloalkyl as well as straight alkyl. Thus, cyclohexyl and others are included.

"Alkenyl" refers to monovalent straight or branched aliphatic radicals which may be derived from alkenes by the removal of one hydrogen, and have the general formula $C_nH_{2n-1}$. Alkenyl substituents may have from 1 to about 30 carbons, more practically 1 to about 20. "Lower alkenyl" refers to alkenyls having from 1 to about 6 carbons. "Olefinic" is a synonym for alkenyl.

As used herein, "alkylene" refers to a divalent straight or branched chain spacer group containing less than 30 carbon atoms, including but not limited to, —$CH_2$—, —$CH(CH_3)$—, —$CH(C_2H_5)$—, —$CH(CH_3)CH_2$—, —$(CH_2)_3$—, and the like. Generally, an alkylene spacer group is aliphatic.

"Aryl" refers to a monovalent radical derived from aromatic hydrocarbons by the removal of one hydrogen. Aryl substituents having ring structures, such as those of phenyl and naphthyl. Typically, aryl substituents are planar with the $\pi$ electron clouds of each carbon remaining on opposite sides of the plane.

Although alkyl, alkenyl and aryl are generally limited to groups having no atoms other than carbon and hydrogen (i.e. no heteroatoms), the invention is not so limited. Heteroatoms, especially oxygen and sulfur, can be present in "R" groups to form "oxa" and "thia" analogs, respectively. However, because of the anticipated elimination, it is desirable to avoid oxa analogs having an oxygen atom 2 carbons removed from the point of monovalency where the R group is attached to the molecule of interest. Exemplary oxa analogs include alkoxy, such as t-butoxy, isopropyloxy and ethoxy, phenoxy and ether substituents.

As used herein, "substituted" refers to the presence of moieties covalently bonded to the "R" groups, including, but not limited to, halide (especially Br and Cl), nitro, lower alkoxy (having from 1-6 carbon atoms, especially methoxy and ethoxy), lower alkyl (having from 1-6 carbon atoms, especially methyl and ethyl), hydroxy, and amino (protecting group may be required). Subject to constraints imposed by the desired solubility, and hydrophobicity of the desired compound, and by the steric constraints or organic chemistry principles, the substituting groups may be placed anywhere, and in any number, on the R group. Some specific substitutions include: Alkaryl, which refers to a monovalent aryl radical bearing alkyl substituents where the aryl radical includes the point of monovalency (e.g. toluyl); and Aralkyl, which refers to monovalent alkyl radicals bearing aryl substituents. In this latter case, the alkyl radical includes the point of monovalency. Benzyl is an example of an aralkyl group.

As used herein, "sterically bulky" refers to substituents groups which occupy a relatively large volume. Aryl groups having five or more carbons are considered "sterically bulky", as are substituted aryl groups. Alkyl and alkenyl groups are "sterically bulky" when they possess at least 4 carbons and are arranged in a branched configuration, the more branches, the bulkier. Any alkyl occupying a volume equal to or larger than t-butyl; and any aryl occupying a volume equal to or larger than phenyl, is considered "sterically bulky". Thus, neopentyl, neohexyl and others meet this description.

"Hydrophobic" refers generally to compounds which are relatively insoluble in aqueous solutions and will not substantially mix with water. Specifically, a compound is deemed hydrophobic if it has a partition coefficient of 0.51 or greater to octanol in a water/octanol partitioning test.

B. Silyl Alcohol Synthesis

Silyl alcohols prepared by any method may be useful in the inventions described below. 2-silyl-ethan-1-ols (or $\beta$-silylethanols or silapropanols) are preferred for reasons which will become apparent. It will be readily apparent to those of ordinary skill in the organic chemistry arts that the terms "$\beta$-silylethanol" and "silapropanol" are equivalent and may be used interchangeably. The former method of nomenclature treats the silyl group ($R_3Si$—) as a substituent on the ethanol, while the later method treats the silicon atom as part of the backbone.

Some of the known preparation methods are set forth in the Background of this application. However, one novel method of synthesis is particularly useful and is described here.

Vinylic esters are olefinic esters characterized by the presence of the alkenyl group on one side (the oxygen side) of the ester linkage. They may be represented by the formula:

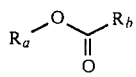

wherein $R_a$ is alkenyl and $R_b$ is H or alkyl, usually lower alkyl, and preferably methyl. In this invention, $R_a$ may be from 2 to about 30 carbons, but more commonly is lower alkenyl. Examples of such esters useful in the invention include vinyl acetate, isopropenyl acetate, butenyl acetate, pentenyl acetate, and etc. Esters wherein the double bond is in the terminal position are preferred, especially vinyl acetate.

Hydrosilation of such esters using a silane of the formula $R_3SiH$ in the presence of a metal catalyst adds H and a silyl group ($R_3Si$—) across the double bond of the alkenyl group $R_a$. Hydrosilation requires a silane, preferably bearing alkyl, aryl, substituted alkyl, or substituted aryl as the "R" groups. Any "R" group of the silane may also independently include halogen and/or oxa or thia analogs of alkyl, aryl and substituted alkyl or aryl. There may be one, two or three "R" groups on the silane. For the uses described below, bulky, hydrophobic substituents are preferred. Phenyl, t-butyl, neopentyl, etc, are exemplary bulky groups.

Metal catalysts useful for hydrosilation include transition-metal complexes, particularly those of cobalt, nickel, platinum, palladium and rhodium, although others may work as well. Specific complexes include $Co_2(CO)_8$; $H_2PtCl_6$; $\{RhCl(CO)_2\}_2$; and others given in Table 6.5 of Collman et al., supra.

Catalytic hydrosilation can be performed under the following conditions. The molar ratio of acetate to silane can range from about 30:1 to about 1:2, and is preferably about 1:1. Intermediate ratios, such as 10:1 or 2:1, are contemplated as well. The metal catalyst may be present in mole percentages ranging from about 0.01% to about 3%, preferably between about 0.2% and about 2%. Lower percentages may require longer reaction times or higher temperatures. For {RhCl(CO)$_2$}$_2$ an optimal mole % is between about 0.25% and about 1.0%. For other catalysts, the optimal concentrations can be obtained from the literature or from routine experimentation. The reaction is best run at room temperature for about 50–70 hours, preferably not longer than 2 weeks. It may, however, proceed more quickly at elevated temperatures; for example, in less than 24 hours at 82° C. The principle reagents should be present at a concentration ranging from neat in vinyl acetate to 4M in toluene; preferably about 1M in toluene. Other reaction conditions for this catalytic step can be found in Collman, et al., which is incorporated by reference.

In hydrosilation, two major products result because the silyl substituent may bond to either side of the double bond to give both 1- and 2- substituted products. If necessary, these can be separated and purified by chromatography, for example, silica based chromatography such as flash column or HPLC. However, in a specific instance, purification is greatly simplified. When vinyl acetate is used as the ester, two products are again obtained as follows:

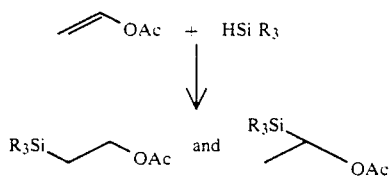

Upon hydrolysis in mild aqueous or alcoholic base, the acetate is converted to an alcohol. However, the 1-silyl substituted alcohol is unstable and spontaneously undergoes a Brook rearrangement (A. G. Brook, *Accounts Chemical Research*, 7:77 (1974)) to give:

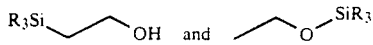

The 2-silyl substituted alcohol does not undergo this rearrangement. Since the 2-silyl substituted product behaves as an alcohol, while the silyl ether behaves as an ether, the two products are easily separated on the basis of these properties using silica gel chromatography, especially HPLC. As will be seen from the examples which follow, this hydrolysis reaction can be run in the same vessel without any intermediate purification of the acetate.

The conditions of hydrolysis preferably are carefully controlled. It will be recalled that 2- or β- substituted intermediates in the anionic form will undergo fragmentation to the silanol as described in the Background section. However, reaction conditions can be selected which will minimize the formation of the undesired product. First, a mild base is selected, preferably one having a pK$_b$ between about 3 and 8. Acceptable bases include the sodium or potassium salts of H$_2$BO$_3$−, HPO$_4$$^{2-}$, SO$_3$$^{2-}$, HCO$_3$− and CO$_3$$^{2-}$. A mild base, having only a weak tendency to dissociate, tends to keep anionic species protonated moreso than strong bases or hydrides (e.g. LiAlH$_4$) taught in the prior art.

The base should be present in a base:acetate molar ratio of from about 0.01:1 to about 3:1, preferably between 0.1:1 and 2.5:1, most preferably between 1:1 and 2:1. The reaction generally takes from 0.5 to 24 h, but preferably takes about 1 hour. In addition, solvents can be selected to minimize the formation of undesired product. For example, the solubility of the base in a particular solvent will affect its strength. It is desirable to have a substantial amount of the base insoluble so as to buffer the ionization equilibrium going on in solution. Also, protic solvents are preferred over aprotic solvents, due to their ability to quench the formation of anionic species. Suitable protic solvents include water, methanol and ethanol. Although the reaction will work in an aqueous medium, it is preferable to use methanol as the solvent.

Silyl alcohols synthesized by this method, as well as silyl alcohols synthesized by other processes, find utility in the synthesis of phosphorylating reagents and protecting agents as described in a later section.

C. Silyl Alcohols

While the above-described method may be used to synthesize many silyl substituted alcohols, one class of silyl alcohols is of particular interest. Previous methods have not been known to synthesize silyl alcohols having three large, bulky groups bonded to the silicon. This is because the principal prior art method of synthesis—i.e., via vinyl silanes as taught by Kumada, et al and Seyferth, supra—requires vinyl silane reagents appropriately substituted with the necessary bulky groups. Presumably due to steric considerations, bulky vinyl silanes are not readily available or easily synthesized. Although triphenyl silane is known (see Lesage, et al. supra), such a bulky silane has not been associated with a vinyl radical to make the bulky vinyl silane.

However, sterically bulky silyl alcohols can be made by the above described method, and have the general formula:

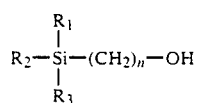

wherein R$_1$, R$_2$ and R$_3$ are independently selected from sterically bulky groups like aryl (e.g. phenyl and naphthyl), substituted aryl (e.g. methoxyphenyl, or nitrophenyl) aralkyl (e.g. triphenylmethyl), alkaryl and alkyl or substituted alkyl having at least 4 carbons in a branched chain (e.g. t-butyl, neopentyl, neohexyl, cyclohexyl, 3-pentyl and 3-ethyl-3-pentyl). In the formula above, n is an integer from 2 to about 20, usually 2 to about 6 and most preferably 2. Exemplary compounds are listed in the table below, although this is by no means an exhaustive list.

TABLE 2

| Illustrative Novel Silyl Alcohols | | | |
|---|---|---|---|
| R$_1$ | R$_2$ | R$_3$ | n |
| phenyl | phenyl | phenyl | 2 |
| phenyl | phenyl | phenyl | 6 |
| phenyl | phenyl | t-butyl | 2 |
| phenyl | t-butyl | t-butyl | 2 |
| phenyl | naphthyl | neopentyl | 2 |
| t-butyl | t-butyl | neopentyl | 2 |
| phenyl | naphthyl | t-butyl | 2 |
| phenyl | t-butyl | neohexyl | 2 |
| phenyl | phenyl | phenyl | 3 |
| phenyl | phenyl | t-butyl | 3 |
| t-butyl | t-butyl | phenyl | 3 |
| phenyl | naphthyl | neopentyl | 3 |
| t-butyl | t-butyl | neopentyl | 3 |
| phenyl | naphthyl | t-butyl | 3 |

TABLE 2-continued

| Illustrative Novel Silyl Alcohols | | | |
|---|---|---|---|
| $R_1$ | $R_2$ | $R_3$ | n |
| phenyl | t-butyl | neohexyl | 3 |

For reasons which will become apparent, substituted bulky groups preferably are substituted with nonpolar substituents.

As mentioned, silyl alcohols find utility in preparing phosphorylating agents and protecting agents. These are described in detail below.

D. Phosphorylating Reagents

Many types of reagents can phosphorylate—i.e. put a phosphate group on the end of—an oligonucleotide. Generally these reagents are classified as phosphotriester reagents, phosphonate reagents (Hydrogen or Alkyl) and phosphoramidite reagents. The mechanisms by which each of these reagents phosphorylate an oligonucleotide is described in the literature.

A novel phosphorylating reagent is represented by the formula:

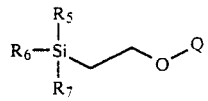

wherein $R_5$, $R_6$ and $R_7$ are independently selected from H, alkyl, aryl, substituted alkyl, substituted aryl, oxa and thia analogs of alkyl, aryl, substituted alkyl and substituted aryl, and halogen; and wherein Q represents a moiety selected from the group consisting of phosphoramidites, alkyl phosphonates, hydrogen phosphonates and phosphotriesters.

For a phosphoramidite, Q has the formula:

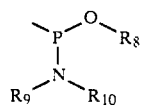

and $R_8$ is generally selected from the group consisting of 2-cyanoethyl, methyl, ethyl, 2-alkylsulfonylethyl, 2-(p-nitrophenyl)ethyl, 2-(9-fluorenyl)ethyl, 2-(2-anthraquinonyl)ethyl, 2-alkylthioethyl, 2-arylthioethyl, 2-trihalomethylethyl, 2-phenylethyl and 2-(2-naphthyl)ethyl. $R_9$ and $R_{10}$ are generally selected independently from H, or straight or branched alkyl having from 1–6 carbons. In a very common phosphoramidite moiety, $R_8$ is 2-cyanoethyl while $R_9$ and $R_{10}$ are both isopropyl.

The novel silyl phosphoramidite may be prepared in a conventional manner by reacting a chlorophosphoramidite with a silyl substituted alcohol. See, e.g., Koster *Tetrahedron Letters*, 24:5843 (1983) which is incorporated herein by reference. Here, it is preferred to use a 2-silyl-ethan-1-ol. The reaction conditions are well known from the literature.

For a phosphotriester reagent, Q has the formula:

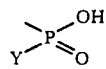

For hydrogen phosphonate or alkyl phosphonate reagents, Q has the above formula, but Y is H or alkyl, respectively.

E. Methods Using Phosphorylating Agents

The above-described phosphoramidite, phosphotriester and phosphonate reagents can be used in a method for phosphorylating an oligonucleotide, particularly an oligonucleotide synthesized on a solid support. It will be realized by those of ordinary skill in the art that a single nucleoside could equally well be phosphorylated in this manner, as could longer polynucleotides. For simplicity, it will be understood that the term "oligonucleotide" will include structures having from one to several hundred nucleoside subunits.

Many methods are known in the literature for synthesizing oligonucleotides and the particular method employed is not relevant to the present invention. Generally, however, automated synthesis is preferred and may be performed using commercial instruments such as an ABI 380A Synthesizer or a Milligen 8700 Synthesizer.

The reaction steps employed by such automated synthesizers are generally known in the art and need not be repeated here. However, it will be noted that when a phosphoramidite or H phosphonate reagent is used, the resulting intermediate is a trivalent phosphite. It is subsequently oxidized to the biologically useful pentavalent phosphate. This oxidation step is readily achieved using, for example iodine, in the automated synthesis process.

A major advantage of the present invention is that the phosphorylation step can be accomplished in the same instrument as synthesis, without removal of the oligonucleotide from the support. Alternatively, oligonucleotides synthesized by other methods (e.g. enzymatic) may be phosphorylated by the methods of the present invention, provided the amino and hydroxy functions present can be protected.

While known methods of phosphorylating have been described in the Background section, none use silyl reagents. Any of the phosphorylating reagents prepared in the preceding section, may be used to phosphorylate an oligonucleotide according to the invention. The methods and conditions are conventional, although the reagents are not. The examples provide further details but the method generally comprises reacting the 5' hydroxyl of an oligonucleoside with a phosphorylating reagent described above, ultimately to form a phosphodiester protected by the silyl group.

The silyl protected, phosphorylated intermediate has the structure:

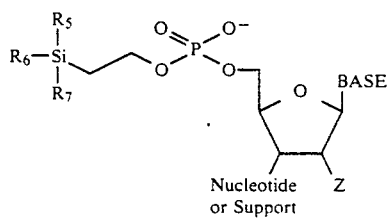

where $R_5$, $R_6$ and $R_7$ are selected as before; Z is H or OH; and BASE represents one of the nucleic acid bases A, C, G, T or U, or analogs thereof. The terminal nucleoside may be attached at its 3' carbon to a support (in the case of phosphorylating a single nucleoside) or, more likely, to a string of one or more other nucleosides (to form an oligonucleotide). Generally, such a string of nucleosides will be connected via phosphodiester linkages, although other linkages are possible (e.g. alkyl phosphonate neutral probes). Obviously, where Z is H, the nucleoside is a deoxyribonucleoside; where Z is OH, it is a ribonucleoside. Analogs of the bases A, C, G, T or U are compounds which, when incorporated into an oligonucleotide, will still permit Watson-Crick base pairing with their respective complementary base. Some exemplary base analogs are published in the USPTO Official Gazette at 1114 OG 43, which is incorporated herein by reference.

While the silyl protecting group must be removed for biological use (e.g. template guided ligation) the protected intermediate also has utility. The silyl group, particularly if it is endowed with bulky, hydrophobic substituents $R_5$, $R_6$ and $R_7$, is useful as a "handle" for purifying and separating phosphorylated oligonucleotides from unphosphorylated failure product by chromatography, e.g. HPLC. Provided the R groups are sufficiently hydrophobic, the oligonucleotide bearing the silyl protecting group is easily differentiable from the unphosphorylated, unprotected oligonucleotide, even when the oligonucleotides approach 50-mer lengths. Of course, shorter lengths are also easily separated. This goes a step beyond the known trityl protecting groups which are useful to monitor phosphorylation success, but not to separate or purify product.

If desired, a deprotecting step may follow phosphorylation and/or separation to yield the 5′ terminal phosphate. The deprotecting step is done by any useful method to yield the desired phosphate. A preferred method, especially useful when the silyl substituent is $\beta$ to the oxygen as above, involves reacting the protected phosphodiester with fluoride ion to give the silyl fluoride, ethylene and the terminal phosphate. Tetrabutylammonium fluoride (TBAF) is a useful fluoride ion for removing the silyl protecting group. This reaction is driven by the release of ethylene when the phosphorylating reagent above is used. See, e.g. Grob, *Helv. Chim. Acta*, 38:594 (1955). It is for this reason that 2-silyl-ethan-1-ols ($\beta$ silylethanols) are preferred silyl alcohol reagents (they have two carbons between the silicon and the oxygen of the phosphodiester, thus permitting the Grob elimination of ethylene). Any other length will not be removed in the deprotection step as easily as the $\beta$ silyl-ethanol derivative.

"Protecting" group and "deprotecting" steps refer to the silapropyl substituent attached to the oxygen of the phosphate. This group may or may not afford "protection" in the usual sense from subsequent reactions that would affect the oxygen atom. However, the term is used as a synonym for "handle" because of the ability to separate phosphorylated oligonucleotide from unphosphorylated failure product using the silapropyl group, and because of the subsequent removal of the group to give the desired phosphate.

The inventions herein described will be better understood in view of the following examples which are intended to be illustrative and non-limiting.

EXAMPLES

A. Preparation of Silyl Alcohols

EXAMPLE 1 a) Preparation of 1,1,1-Triphenyl-3-acetoxy-1-silapropane (3)

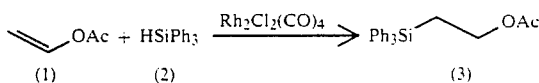

A solution of 3.69 mL (40 mmol) of vinyl acetate (1), 10.42 g (40 mmol) of triphenylsilane (2), and 77.8 mg (0.25 mmol) of $Rh_2Cl_2(CO)_4$ in 40 mL of toluene was stirred at room temperature under $N_2$ for a total of 63 h. Several runs of the reaction at this scale had unpredictable induction periods, followed by rapid heat evolution. Scaleup of this reaction should be done with a cooling bath close at hand. The very dark reaction mixture was treated with 5 g of decolorizing charcoal, and the mixture boiled briefly. After cooling, the mixture was filtered through a 1 cm pad of Celite ™ with filtrate and washings being collected. Solvent was evaporated and the remaining residue was vacuum dried. At this point, the crude material was carried on to the hydrolysis step. NMR analysis showed an $\alpha{:}\beta$ ratio of 1:1.57. The following protocol was carried out for compound identification purposes. A 100 mg sample of crude material was flash chromatographed using 4% EtOAc in cyclohexane on a 25 mm I.D. × 150 mm long silica gel column. This afforded 29 mg of (3) after recrystallization from MeOH, mp 67°–68° C.

IR: ($CDCl_3$, $cm^{-1}$) 3070 (m), 1728 (vs), 1425 (vs), 1249 (vs); MS: ($DCl/NH_3$) m/e 364 (M+$NH_4$);

NMR: (300 MHz, $CD_2Cl_2$) $\partial$7.6–7.3 (m, 15H, phenyl), 4.22 ($B_2$ of $A_2B_2$, 2H, $CH_2O$), 1.87 (s, 3H, $CH_3$), 1.86 ($A_2$ of $A_2B_2$, 2H, $CH_2Si$);

$^{13}C$ NMR: (75 MHz, $CDCl_3$) $\partial$171.1 (C=O), 135.5 (meta), 134 (ipso), 129.7 (para), 128 (ortho), 62.1 ($CH_2O$), 21 (Me), 14.4 ($CH_2Si$).

Elemental Analysis: Calc'd for $C_{22}H_{22}O_2Si$; C: 76.26; H: 6.40. Found; C: 76.45; H: 6.37.

b) Preparation of 1,1,1-Triphenyl-1-silapropane-3-ol (4)

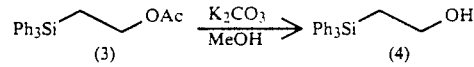

The crude (3) was dissolved in 100 mL MeOH, and 10.0 g of $K_2CO_3$ was added all at once. The reaction was complete after 1 h of stirring at room temperature. The solids were filtered off, and the filtrate was concentrated. The concentrated residue was partitioned between 100/100 mL $H_2O$/EtOAc. After solvent removal from the organic layer, the residue was vacuum dried. Flash chromatography (18% EtOAc in cyclohexane, $R_f$=0.32) using a 41 mm I.D. × 150 mm long silica gel column afforded 3.42 g (28%) of (4). Recrystallization from cyclohexane gave the analytical sample as a snow-white solid, mp 96°–97° C.

IR: ($CDCl_3$, $cm^{-1}$) 3616 (m), 2970 (m), 1429 (vs);
MS: (FAB/DMF-Kl) m/e 343 (M+K);
NMR: (300 MHz, $CD_3OD$) $\partial$7.55–7.3 (m, 15H, phenyl), 3.73 ($B_2$ of $A_2B_2$, 2H, $CH_2O$), 1.78 ($A_2$ of $A_2B_2$, 2H, $CH_2Si$);

$^{13}$C NMR: (75 MHz, CDCl$_3$) ∂135.5 (meta), 134.4 (ipso), 129.6 (para), 128 (ortho), 59.8 (CH$_2$O), 18.7 (CH$_2$Si).

Elemental Analysis: Calc'd for C$_{20}$H$_{20}$OSi.0.2 H$_2$O; C:77.98; H: 6.67. Found; C: 77.92; H: 6.62.

EXAMPLE 2 a) Preparation of 1,1-Dimethyl-1-phenyl-3-acetoxy-1-silapropane

To a solution of 6.13 mL (40 mmol) of PhMe$_2$SiH and 3.69 mL of vinyl acetate in 40 mL of toluene was added 61.3 mg (0.16 mmol) of Rh$_2$Cl$_2$(CO)$_4$. Immediately, the reaction evolved heat and gas. Within 5 min, the golden yellow reaction had turned dark brown in color. After 1 h, the reaction was complete. The reaction was worked up as in example 1a to give 8.39 g of crude adduct. Proton NMR analysis showed an α:β addition ratio of 1.44:1.0. A 100 mg sample was purified by flash chromatography as in example 1a to give 28 mg of the title compound as a colorless oil.

IR: (CDCl$_3$, cm$^{-1}$) 2960 (m), 1724 (vs), 1426 (m), 1255 (vs);

MS: (DCl/NH$_3$) m/e 240 (M+NH$_4$);

NMR: (300 MHz, CDCl$_3$) ∂7.6–7.3 (m, 5H, phenyl), 4.18 (B$_2$ of A$_2$B$_2$, 2H, CH$_2$O), 1.99 (s, 3H, Me), 1.25 (A$_2$ of A$_2$B$_2$, 2H, CH$_2$Si), 0.35 (s, 6H, SiMe);

$^{13}$C NMR: (75 MHz, CDCl$_3$) ∂171.1 (CO), 138 (ipso), 133.4 (meta), 129.2 (para), 127.9 (ortho), 62.3 (CH$_2$O), 21.1 (Me), 16.5 (CH$_2$Si), −2.9 (SiMe).

Elemental Analysis: Calc'd for C$_{12}$H$_{18}$O$_2$Si; C: 64.82; H: 8.16. Found; C: 65.02; H: 8.07.

b) Preparation of 1,1-Dimethyl-1-phenyl-1-silapropane-3-ol

The remaining 8.29 g of crude product from part b, above, was worked up as in the case of example 1 to give 1.64 g of 1,1-dimethyl-1-phenyl-1-silapropane-3-ol as a colorless oil, 23% overall.

IR: (CDCl$_3$, cm$^{-1}$) 3616 (m), 2960 (m), 1425 (m), 1251 (s);

MS: (DCl/NH$_3$) m/e 198 (M+NH$_4$);

NMR: (300 MHz, CDCl$_3$) ∂7.6–7.3 (m, 5H, phenyl), 3.75 (B$_2$ of A$_2$B$_2$, 2H, CH$_2$O), 1.49 (s, 1.2H, OH), 1.22 (A$_2$ of A$_2$B$_2$, 2H, CH$_2$Si), 0.33 (s, 6H, SiMe);

$^{13}$C NMR: (75 MHz, CDCl$_3$) ∂138.5 (ipso), 133.4 (meta), 129 (para), 127.8 (ortho), 59.9 (CH$_2$O), 21.1 (CH$_2$Si), −2.8 (SiMe).

Elemental Analysis: Calc'd for C$_{10}$H$_{16}$OSi.0.1 H$_2$O; C: 65.92; H: 8.99. Found; C: 65.95; H: 8.97.

EXAMPLE 3 a) Preparation of 1,1,1-Triethyl-3-acetoxy-1-silapropane

To a solution of 6.39 mL (40 mmol) of Et$_3$SiH and 3.69 mL (40 mmol) of vinyl acetate in 40 mL of toluene is added 61.3 mg (0.16 mmol) of Rh$_2$Cl$_2$(CO)$_4$. Caution: the reaction evolves heat and gas. Within about 5 min, the reaction mixture darkens in color. Reaction is judged complete by TLC analysis (10% EtOAc in cyclohexane) after 1 h. The reaction is worked up and purified, if desired, as in example 1a.

b) Preparation of 1,1,1-Triethyl-1-silapropane-3-ol

The crude product from part a) can be worked up as in the case of triphenylsilylethanol (example 1) to give the 1,1,1-triethyl-1-silapropane-3-ol.

EXAMPLE 4

Preparation of 1,1,1-Triphenyl-1-silaheptane-7-ol (5)

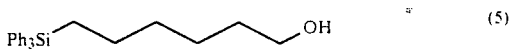

The acetate of 5-hexen-1-ol is prepared by refluxing 4.8 mL (40 mmol) of the alcohol in 15/15 mL of pyridine/acetic anhydride for 4 h. The solvents are removed in vacuo, and the residue is thoroughly vacuum dried. The crude acetate is dissolved in 40 mL of toluene, and 10.42 g of triphenylsilane is added, followed by 77.8 mg (0.25 mmol) of Rh$_2$Cl$_2$(CO)$_4$. The reaction is stirred at room temperature under N$_2$ for 24 h, during which time the reaction turns dark brown in color. Some quantities of the isomer 2-methyl-1,1,1 triphenylsilahexan-6-ol can be expected. If necessary, the isomers can be separated by chromatography. Workup as in example 1a, followed by base hydrolysis as in 1b, affords the title compound, (5).

B. Preparation of Phosphorylating Reagents

EXAMPLE 5

Preparation of 2-Trimethylsilylethyl-2-cyanoethyl-N,N-diisopropylaminophosphoramidite (1)

To a solution of 573 μL (4 mmol) of 2-trimethylsilylethanol (commercially available from Aldrich Chemical, Milwaukee, Wis.; or prepared in a manner analagous to example 2, above) and 1.39 mL (8 mmol) of i-Pr$_2$NEt in 8 mL of THF at 0° C. was added 892 μL (4 mmol) of 2-cyanoethyl-N,N-diisopropylaminochlorophosphoramidite all at once. The reaction became very cloudy almost immediately. The ice bath was removed, and the reaction stirred to room temperature overnight, for a total of 19 h. After filtration to remove i-Pr$_2$NEt-HCl, the THF was evaporated. The residue was partitioned between 50/50 mL EtOAc/0.1M Na$_2$CO$_3$, pH 12. After phase separation and solvent removal of organic phase, the residue was vacuum dried. Flash chromatography using 12% EtOAc in cyclohexane on a 150 mm×25 mm ID column afforded 573.8 mg (78%) of the title compound as a water-white viscous oil, R$_f$=0.65 in 15% EtOAc in cyclohexane.

MS: (DCl, NH$_3$) 319 (M+H), 291 (M-HCN);

NMR: (CD$_2$Cl$_2$) ∂3.9–3.62 (m, 4H), 3.56 (dsept, 2H, J$_{CH}$=7.0 Hz, J$_{PH}$=10.0 Hz, NH), 2.59 (t, 2H, J=6.2 Hz, CH$_2$CN), 1.15 (dd, 12H, J$_{CH}$=7.0, J$_{PH}$=2.2 Hz, Me), 0.97 (tq, 2H, J=8.0, 0.7 Hz, CH$_2$Si), 0.03 (s, 9H, SiMe).

EXAMPLE 6

Preparation of 2-Triphenylsilylethyl-2-cyanoethyl-N,N-diisopropylaminophosphoramidite (6)

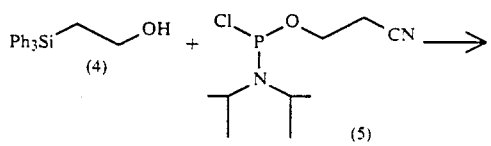

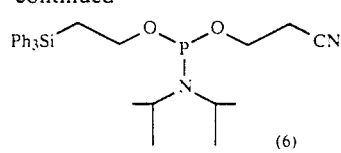

(6)

To a solution of 3.04 g (10 mmol) of (4), 4.18 mL (24 mmol) of i-Pr$_2$NEt, and 5 mg of 4,4-dimethylaminopyridine in 15 mL of THF at 0° C. was added 2.68 mL (12 mmol) of 2-cyanoethyl-N,N-diisopropylaminochlorophosphoramidite (5) all at once. A white precipitate formed almost immediately. Reaction was complete after 30 min at 0° C. After solvent removal, the residue was partitioned between 100/100 mL 0.1M Na$_2$CO$_3$./EtOAc, and the phases separated. The aqueous phase was re-extracted with 50 mL EtOAc, and the combined organic phases were concentrated and vacuum dried. Flash chromatography (10% EtOAc in cyclohexane) using a 41 mm I.D.×150 mm long silica gel column gave 3.35 g of (6) (66%) after vacuum drying overnight as a viscous colorless oil. This material gradually crystallized in a −20° C. freezer over the course of several weeks. During the chromatography, 100 μL NEt$_3$ was added to each fraction, in order to minimize the effects of adventitious acid in the fraction tubes or in the silica gel used for flash chromatography.

IR: (film, cm$^{-1}$) 2962 (m), 1426 (m);
MS: (DCl/NH$_3$) m/e 505 (M+H);
NMR: (300 MHz, CD$_3$CN) δ7.6–7.3 (m, 15H, phenyl), 3.9–3.7 (m, 2H, CH$_2$O), 3.66 (dt, 2H, J$_{CH}$=5.9 Hz, J$_{PH}$=7.7 Hz, CH$_2$O), 3.51 (dsept, 2H, J$_{CH}$=6.6 Hz, J$_{PH}$=9.9 Hz, NH), 2.54 (t, 2H, J=5.5 Hz, CH$_2$CN), 1.87 (br t, 2H, J=6.3 Hz, CH$_2$Si), 1.07 (dd, 12H, J$_{CH}$=6.6 HZ, J$_{PH}$=29.4 Hz, Me);
$^{13}$C NMR: (75 MHz, CD$_3$CN) δ136.3 (meta), 135.5 (ipso), 130.7 (para), 129 (ortho), 117.7 (CN), 61.1 (d, J$_{PC}$=18.3 Hz, CH$_2$O), 59.3 (d, J$_{PC}$=18.3 Hz, CH$_2$O), 43.6 (d, J$_{PC}$=12.2 Hz, NCH), 24.8 (virtual t, J$_{PC}$=7.3 Hz, Me), 21 (d, J$_{PC}$=7.3 Hz, CH$_2$CN), 17.2 (d, J$_{PC}$=7.3 Hz, CH$_2$Si);
$^{31}$P NMR: (202 MHz, CD$_3$CN) δ145.6.

EXAMPLE 7

Preparation of 2-Triethylsilylethyl-2-cyanoethyl-N,N-diisopropylaminophosphoramidite Example 5 is repeated except the product of example 3b is used as the starting compound to produce the title compound.

EXAMPLE 8

Preparation of 2-bismethylphenylsilylethyl-2-cyanoethyl-N,N-diisopropylaminophosphoramidite Example 6 is repeated except the product of example 2b is used as the starting compound to produce the title compound.

EXAMPLE 9

Preparation of Triphenylsilylethyl H-phosphonate-DBU reagent

To a solution of N-methylmorpholine (89 equiv), triazole (33 equiv) and PCl$_3$ (10 equiv) is added triphenylsilylethanol at 0° C. The reaction is stirred at this temperature for 2.5 h. The reaction is then quenched by addition of 100 mM 1,5-diazabicyclo [5.4.0] undec-5-ene (DBU)-bicarbonate, and the phases are separated. The organic phase is stripped to dryness in vacuo, and the crude H-phosphonate-DBU is purified by chromatography.

C. Preparation of Phosphorylated, Protected Oligonucleotides and Deprotection Thereof

EXAMPLE 10 a) Use of (6) in Automated Phosphorylation of DNA

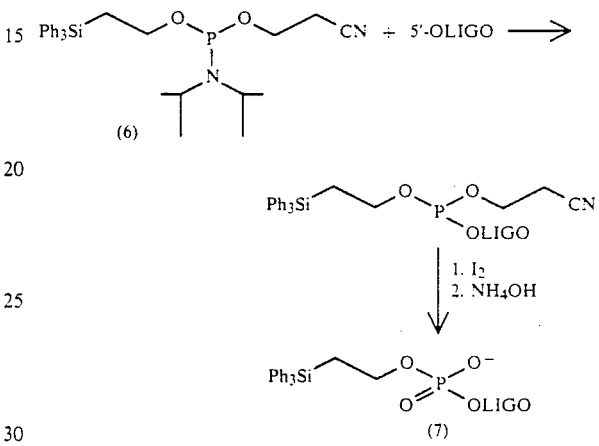

The phosphoramidite (6) (example 6, above) was used to phosphorylate a 25-mer oligonucleotide at the 1 μmol level using an ABI (Foster City, Calif.) 380A DNA Synthesizer. The phosphoramidite couplings were run using the synthesis program from the manufacturer except that the "wait" time (time of contact of phosphoramidite solution with support) and "wash" time are both doubled. The preparative HPLC run, showing separation of the failure sequences from full-length oligo, is shown in FIG. 1.

b) Deprotection of Phosphorylated Oligonucleotide

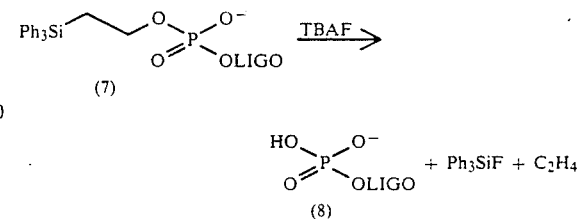

Figure 2:
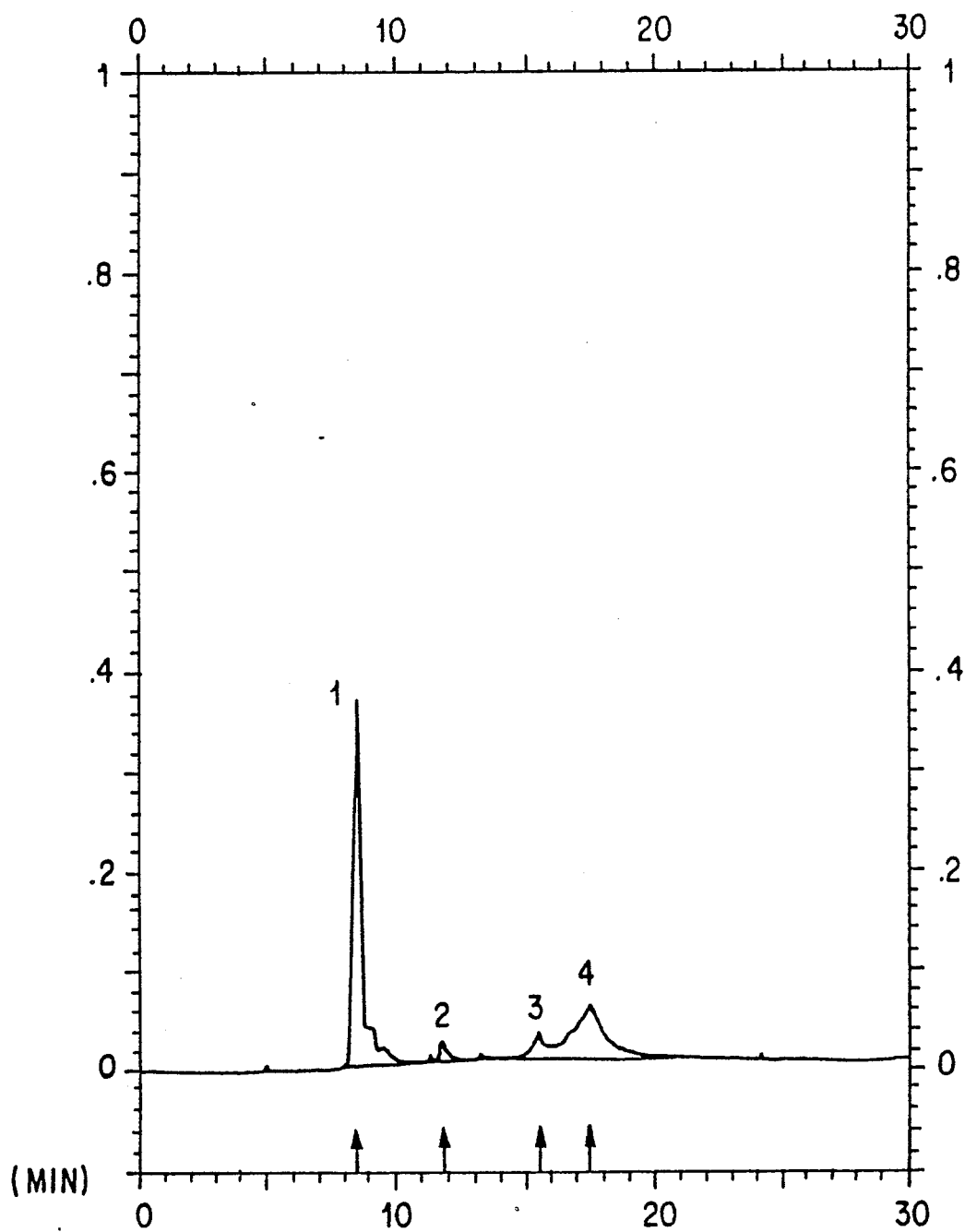
FIG. 2 is a chromatogram showing separation of deprotected, phosphorylated oligonucleotide (peak 1 at 8.4 min) from other products (e.g. silylfluorides). The conditions are the same as in FIG. 1. (See Example 9b.)

The collected material (7) from part a) was dried in vacuo, then ethanol precipitated. The purified DNA was then desilylated using 100/100 μL of DMSO/1.0M Tetra-n-butyl ammonium Fluoride (TBAF) (Aldrich, Milwaukee, Wis.). The reaction was performed in a 68° C. heating block for 3.5 h. The reaction was diluted to 500 μL with 300 μL of water, and the reaction was desalted by passage down a NAP-5 column (Pharmacia, Piscataway, N.J.). The 1.0 mL eluate was dried in vacuo, then was ethanol precipitated to give purified, terminally phosphorylated DNA. HPLC analysis of this material is shown in FIG. 2.

EXAMPLE 11

Example 10 is repeated except the phosphoramidite reagent of example 5 is used in place of the phosphoramidite reagent of example 6.

EXAMPLE 12

Example 10 is repeated except the phosphoramidite reagent of example 7 is used in place of the phosphoramidite reagent of example 6.

EXAMPLE 13

Example 10 is repeated except the phosphoramidite reagent of example 8 is used in place of the phosphoramidite reagent of example 6.

EXAMPLE 14

Phosphorylation by the H-phosphonate method

The reagent from Example 9 is used to phosphorylate an oligonucleotide using the general reaction protocol and conditions of Froehler, et al., *Tetrahedron Letters*, 27:469-472 (1986) except the coupling reagent is adamantoyl chloride and the capping reagent is β-cyanoethyl hydrogen phosphonate. After adamantoyl chloride catalyzed coupling of the 5'-hydroxyoligonucleotide with the triphenylsilylethyl hydrogen phosphonate is complete, all H-phosphonate linkages in the oligonucleotide are oxidized with iodine to the phosphodiester oxidation state. The oligonucleotide obtained can be separated on HPLC in the same manner as DNA of identical sequence which is prepared using phosphoramidite chemistry. This material may be desilylated in the same fashion as the phosphoramidite-prepared oligonucleotide.

What is claimed is:

1. A process for synthesis of silyl alcohols, comprising:

a) hydrosilation of an vinylic ester of the formula

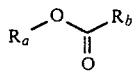

wherein $R_a$, is a straight or branched alkenyl group having from 2 to about 20 carbons and $R_b$ is H or lower alkyl, with a silane of the formula

wherein $R_5$, $R_6$ and $R_7$ are independently selected from the group consisting of H, alkyl, aryl, substituted alkyl, substituted aryl, oxa and thia analogs of alkyl, aryl, substituted alkyl and substituted aryl, and halogen, in the presence of a metal catalyst capable of catalyzing the addition of H and a silyl group across the double bond of the alkenyl group to form a silyl substituted ester; and b) hydrolyzing the silyl substituted ester to an alcohol in the presence of mild base.

2. The process of claim 1 wherein $R_a$ is lower alkenyl.

3. The process of claim 2 wherein $R_a$ is vinyl.

4. The process of claim 1 wherein $R_b$ is lower alkyl.

5. The process of claim 4 wherein $R_b$ is methyl.

6. The process of claim 1 wherein at least one of $R_5$, $R_6$ and $R_7$ consists of a sterically bulky group.

7. The process of claim 6 wherein each of $R_5$, $R_6$ and $R_7$ consists of a sterically bulky group.

8. The process of claim 1 wherein at least one of $R_5$, $R_6$ and $R_7$ consists of a hydrophobic group.

9. The process of claim 8 wherein each of $R_5$, $R_6$ and $R_7$ consists of a hydrophobic group.

10. The process of claim 1 wherein hydrosilation is done in a solution of toluene ranging from about 0.1 to about 4 molar.

11. The process of claim 10 wherein said solution is about 1 molar.

12. The process of claim 1 wherein said metal catalyst is a transition metal complex having a metal selected from the group consisting of cobalt, nickel, platinum, palladium and rhodium.

13. The process of claim 12 wherein said metal catalyst is $\{RhCl(CO)_2\}_2$.

14. The process of claim 1 wherein said hydrolysis is done in a protic solvent.

15. The process of claim 1 wherein said mild base is an alcoholic solution of $K_2CO_3$.

16. The process of claim 15 wherein said $K_2CO_3$ is present in base:acetate molar ratio of between 0.1:1 and 2.5:1.

17. The process of claim 14 wherein said protic solvent is methanol.

18. The process of claim 1, further comprising a step of separating the silyl substituted alcohol from undesired products of side reactions.

* * * * *